United States Patent [19]
Kauffman et al.

[11] Patent Number: 5,933,016
[45] Date of Patent: *Aug. 3, 1999

[54] SINGLE ELECTRODE CONDUCTIVITY TECHNIQUE

[75] Inventors: Robert E. Kauffman, Centerville; James D. Wolf, Kettering, both of Ohio

[73] Assignee: The University of Dayton, Dayton, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/707,965

[22] Filed: Aug. 30, 1996

[51] Int. Cl.⁶ .................................................. G01R 27/22
[52] U.S. Cl. ..................... 324/698; 324/446; 73/53.05
[58] Field of Search ................... 324/439, 442, 324/446, 693, 694, 698, 717, 722, 724; 340/631, 603; 73/53.05

[56] References Cited

U.S. PATENT DOCUMENTS

| | | | |
|---|---|---|---|
| 3,876,935 | 4/1975 | Guillermie et al. | 340/631 X |
| 4,029,554 | 6/1977 | Ellison . | |
| 4,146,437 | 3/1979 | O'Keefe . | |
| 4,317,705 | 3/1982 | Hamada et al. . | |
| 4,372,980 | 2/1983 | Luebke et al. . | |
| 4,635,473 | 1/1987 | Hochstein . | |
| 4,646,070 | 2/1987 | Yasuhara et al. | 340/603 |
| 4,654,126 | 3/1987 | Amelio et al. . | |
| 4,686,857 | 8/1987 | Kato | 324/698 X |
| 4,701,713 | 10/1987 | Eaton et al. | 324/439 X |
| 4,744,870 | 5/1988 | Kauffman . | |
| 4,764,258 | 8/1988 | Kauffman . | |
| 4,803,466 | 2/1989 | Gurstein et al. | 340/603 |
| 4,928,065 | 5/1990 | Lane et al. | 324/464 |
| 5,071,527 | 12/1991 | Kauffman | 324/439 X |
| 5,089,780 | 2/1992 | Megerle | 324/698 X |
| 5,485,099 | 1/1996 | Collins et al. | 324/693 X |
| 5,523,692 | 6/1996 | Kuroyanagi et al. | 324/698 X |

FOREIGN PATENT DOCUMENTS

| | | |
|---|---|---|
| 20 27 947 | 6/1970 | Germany . |
| WO 88/01740 | 3/1988 | WIPO . |
| WO 96/08711 | 3/1996 | WIPO . |

OTHER PUBLICATIONS

Le point sur les capteurs by Daniel Mansion, entitle "Mesure de conductivite de liquides" (XP 002047209). (no date).
International Search Report, dated Jan. 5, 1998.

*Primary Examiner*—Michael Brock
*Attorney, Agent, or Firm*—Killworth, Gottman, Hagan & Schaeff, LLP

[57] ABSTRACT

A method and apparatus are disclosed for the analysis of a fluid to determine the remaining useful life of the fluid and whether the fluid has become contaminated. The method can be performed either on-line or off-line, however, the on-line method is preferred. In the method, a sample of the fluid is contacted by a single electrode which is connected to the ground potential by means of the equipment in which the fluid is used. A current is applied to the sample through the electrode and the conductivity of the sample is measured. The conductivity measurement can then compared to known values for the fluid to determine the remaining useful life of the fluid and whether the fluid has become contaminated.

14 Claims, 3 Drawing Sheets

CONDUCTIVITY VERSUS EQUIPMENT OPERATING TIME PLOTS SHOWING EFFECTS OF ACID BUILDUP AND LIQUID CONTAMINATION

SINGLE ELECTRODE CONDUCTIVITY TECHNIQUE

The United States Government has rights in this invention pursuant to Contract No. F33615-92-C-2207 awarded by the Department of the Air Force.

BACKGROUND OF THE INVENTION

The present invention relates generally to a method for evaluating fluids and, more specifically, to a technique employing a single electrode for conductivity analysis, including on-line analysis, of fluids subject to degradation and/or contamination.

Fluids, such as oils, lubricants, cooking oils and other fluids are used in ways that cause their degradation. For example, it is common to lubricate and cool the components of operating equipment by wetting them with an oil or lubricant. As the oil or lubricant carries out these functions, it experiences environmental stresses which cause it to degrade. As another example, oils used as transmission fluids and in hydraulic systems are subjected to stresses such as pressure, frequent movement and heat. As still another example, cooking oils undergo severe thermal-oxidative stresses. The degradation of the base stock can lead to the production of acids within the cooking oil which affect the taste of the food.

Because of this degradation, antioxidants are frequently added to fluids to reduce their rate of degradation. As long as the antioxidant system remains intact, the oxidative degradation of the base stock is minimal, and so are changes in the properties of the fluid. However, the antioxidants in the fluid gradually deplete over time. Eventually, the antioxidants become ineffective allowing changes in the physical properties of the base stock to occur. At that point, the fluid is no longer able to protect the equipment, and its useful life is completed. The continued use of a fluid after its useful life can result in excessive component wear and eventual equipment failure of the equipment in which the fluid is used. In addition, abnormal depletion rates for antioxidants may indicate accelerated fluid oxidation leading to severe wear problems prior to equipment failure.

Not all fluids contain antioxidants. In this case, the degradation of the base stock can lead to the production of acids within the fluid which render it useless. For example, cooking oils become rancid when they degrade past a certain point.

Early detection of liquid contamination is also important, as is early detection of failures in cooking oils. If a liquid from another part of a system leaks into the fluid, the fluid could become useless because of that contamination. For example, if a coolant leaks into the lubrication system of an engine, the lubricating fluid degrades faster than uncontaminated fluid and becomes useless in that engine. Use of a contaminated lubricating fluid can damage the engine if the fluid is not replaced.

Since it is undesirable to use a fluid beyond its useful life, an equipment operator will establish scheduled fluid changes for the equipment. The length of operating time between scheduled changes is chosen conservatively so that a fluid, which is beyond its useful life, does not remain in the equipment and damage the equipment. Unfortunately, this conservative approach results in fluids which still have useful lives being discarded.

The ability to analyze fluids, such as oils, lubricants, cooking oils and other fluids, for antioxidant depletion, oxidation initiator buildup, product buildup and liquid contamination would eliminate the need to perform fluid changes on the basis of a fixed schedule. This would allow longer use of the fluid providing savings in material and labor costs.

U.S. Pat. Nos. 4,744,870 and 4,764,258 to Kauffman, which are both assigned to the assignee of the present invention, disclose methods for determining the remaining useful life of fluids. These methods are fast, accurate, easy to operate and can be performed with inexpensive equipment. In these methods, fluid samples are mixed with a solvent and an electrolyte in either an organic base or a solid substrate, depending on the type of fluid which is being tested. A sample of fluid is removed from the system, placed in an electrolytic cell and subjected to a cyclic voltammetric analysis. The current generated during the cyclic voltammetric analysis is measured and recorded. The remaining useful life of the fluid is then determined from the oxidation or reduction wave height. However, these methods can only be performed off-line and are limited to fluids containing antioxidants.

U.S. Pat. No. 5,071,527, also to Kauffman and assigned to assignee of the present invention, solves the problem cited above by providing a more complete fluid analysis, including on-line analysis, which measures antioxidant depletion, oxidation initiator buildup, product buildup and liquid contamination. The method uses a triangular wave form which is applied to a microelectrode. The resulting current is monitored at a second microelectrode. In high resistance fluids, such as oils, fuels, etc., a third electrode is used as a reference voltage for the applied voltage wave form. This technique uses a voltage range of about ±120V to cause electro-oxidation of antioxidants and electro-reduction of hydroperoxides and other thermal-oxidation products. The current flow produced by the electro-chemical reactions is then used to monitor the remaining useful life of the monitored fluid.

While the technique taught in U.S. Pat. No. 5,071,527 provides a useful and complete fluid analysis, often such an analysis is too extensive and the equipment necessary to conduct such an analysis is expensive. Thus, a need exists for a fluid analysis technique which requires less circuitry and is less expensive, even though it might not be as complete.

SUMMARY OF THE INVENTION

The present invention solves this need by providing a method and apparatus for analysis of fluids, which method and apparatus can be used on-line; although, the unique fluid analysis of the present invention can also be used off-line, if desired. The present invention provides a fluid analysis technique which requires less circuitry and is less expensive than prior art methods. This method and apparatus can be used to measure the remaining useful life of a fluid and to determine whether the fluid is contaminated.

In the method of this invention, an electric potential is applied to an electrode to produce an electric current through a fluid either off-line with a sample of the fluid, on-line with a continuously changing sample or with a sample in an on-line sample reservoir. The method and apparatus of this invention employ a single electrode for analysis of fluids, such as oils, lubricants, cooking oils and other similar fluids subject to degradation and/or contamination. The electrode is electrically connected to the ground potential by the monitored fluid. A square voltage wave is applied to the fluid by an electrode which is in contact with the fluid. The current which flows between the ground potential and the electrode is monitored at the single electrode to determine a current output signal which is rectified and recorded. The current output signal is then analyzed to determine the conductivity of the fluid. Once the conductivity of the fluid is known, one can determine the remaining useful of the fluid and whether the fluid is contaminated. To determine the fluid's remaining useful life and whether it is contaminated, the conductivity of the fluid is compared to known conductivity values for the fluid in its original, uncontaminated state.

The method of this invention employs a square wave form because the square wave form produces a continuous current output signal which eliminates the need for peak hold circuitry required to monitor other wave forms such as triangular wave forms. The voltage of this invention is kept low to insure that the monitored current is derived entirely from the fluid's conductivity and to minimize the current produced by the electrode, chemical activity of antioxidants and thermal-oxidation by-products.

The on-line analysis can involve either a built-in electrode system or a dip-stick type electrode system. In the built-in system, the electrode is permanently attached to a source, such as a return line, of an essentially continuously changing sample of used fluid or to a use container for a fluid, such as a deep fryer. The current measurement and recording in this instance can be performed intermittently at desired intervals or continuously. In the dip-stick type system, the electrode is placed in an on-line sample reservoir (such as an oil pan, deep fryer or portions of such reservoirs) for the used fluid. The electrode is then removed once the analysis is completed.

Other advantages of the present invention will become apparent from the following detailed description, the accompanying drawings and the appended claims.

DETAILED DESCRIPTION OF THE INVENTION

The system of this invention requires minimal circuitry for effective operation. To detect the conductivity of a fluid, a square voltage wave form is applied to the fluid at an electrode conductivity probe which is electrically connected to the ground potential by the monitored fluid. The current that flows between the ground potential and the electrode is also monitored at the single electrode. The square wave form produces a continuous current output eliminating the need for peak hold circuitry.

The conductivity of the sample is measured using the electrode. The conductivity measurements are used to determine the remaining useful life of the fluid and to detect leaks in the fluid system. Once the conductivity measurements have been taken, the results are analyzed. The conductivity values can be compared to previously derived data and to certain preselected values for the fluid. The exact data and values chosen for the comparison depend upon the type of fluid, the type of oxidant in the fluid, fluid consumption rates and other factors. These standard values can be determined by means of testing the specific system being used.

Figure 1:
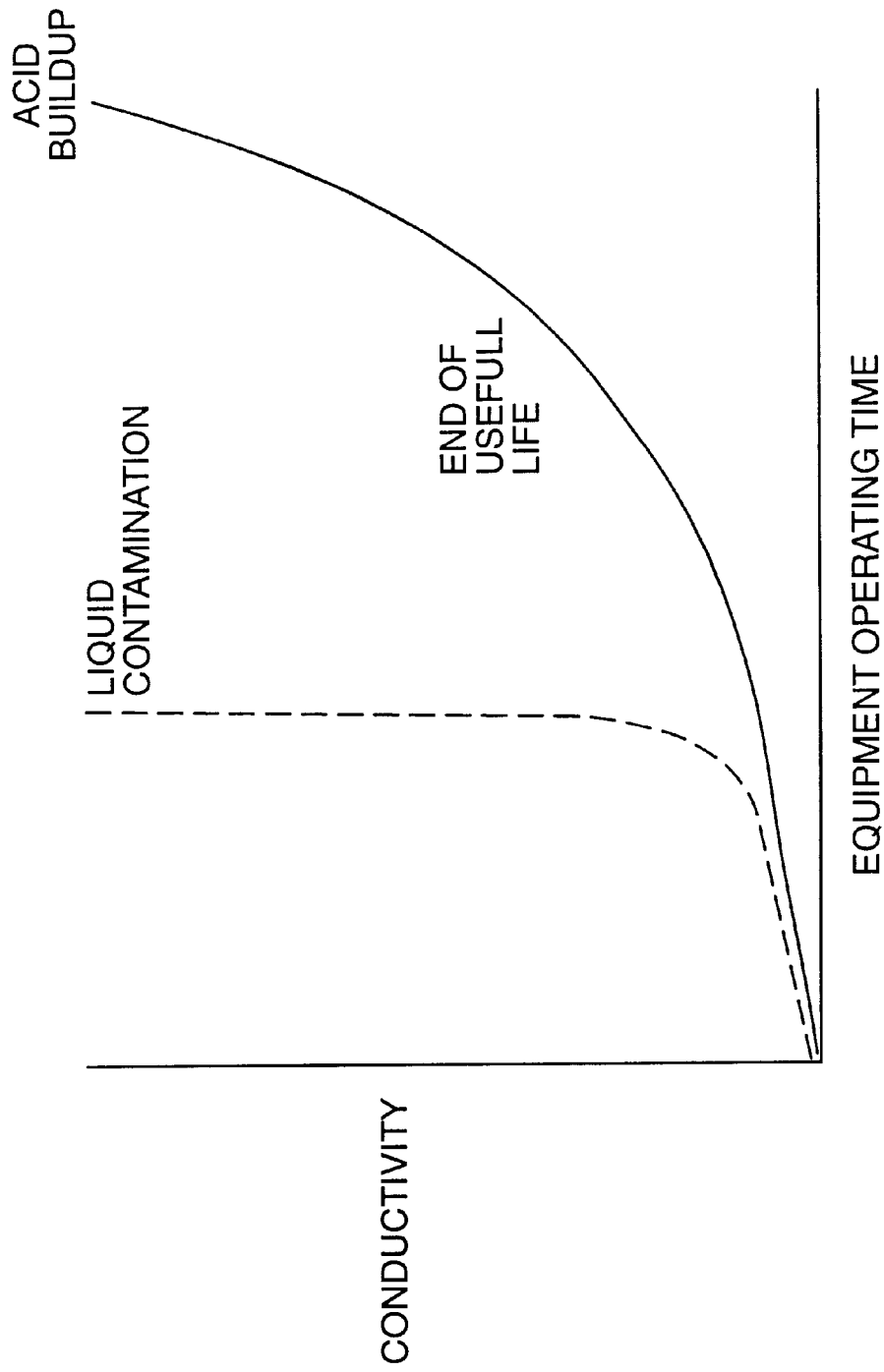
FIG. 1 is a plot of conductivity versus equipment operating time showing the effects of acid buildup and liquid contamination.

FIG. 1 shows simulated plots of the effects of acid buildup and of a coolant leak in a fluid. The plot shows conductivity versus operating time. As can be seen in FIG. 1, a fluid degrades gradually over time. The acid build up in the fluid gradually causes an increase in conductivity of the fluid. When the conductivity of the fluid reaches a certain value, its useful life has ended and the fluid should be replaced.

In contrast to the gradual degradation of a fluid caused by its use over a period of time, a leak in the equipment causes an immediate increase in the conductivity of the fluid. When a coolant leak exists, highly conductive liquids come into contact with the fluid system contaminating the fluid. As can be seen in FIG. 1, once the fluid becomes contaminated, these highly conductive liquids cause a rapid increase in the conductivity of the fluid. Such a rapid increase in the conductivity of the fluid indicates that the fluid has become contaminated and should be replaced. This rapid increase also indicates that the equipment should be checked for the presence of a leak. Thus, by monitoring the conductivity of a particular fluid and comparing that conductivity value to known values, one can determine the remaining useful life for that fluid and/or whether that fluid has become contaminated.

In carrying out the conductivity analysis, the potential is varied from about +20V to about −20V and is then rectified to a positive voltage reading. The voltage of the single electrode conductivity probe is maintained between about ±20 volts to ensure that the monitored current is based entirely on the conductivity of the fluid and not on any oxidation-reduction reactions caused by the current flow. In a preferred embodiment, the voltage of the probe is maintained between about ±10V. The smaller scan rate minimizes the current produced by the electrochemical activity of antioxidants and thermal-oxidation by-products. The frequency of the scan rate can vary between about 1 and about 100 Hertz.

The present system is preferably used to conduct an on-line analysis. The on-line analysis can involve either a built-in electrode system or dip-stick type electrode system. The built-in system has the advantage of analyzing the fluid in use or on its return before it is diluted in a reservoir. This system is more sensitive to abnormal operating conditions than the dip-stick electrode system, which monitors the fluid in a sample reservoir. With the built-in electrode, the condition of the fluid can be monitored intermittently at various intervals or continuously. On the other hand, the dip-stick electrode does not require any modification to the equipment, from which the fluid sample is extracted, prior to use. In addition, the dipstick can be cleaned and checked between uses to eliminate the effects of electrode filming, erosion or other problems which may have an effect on the long term accuracy of the built-in electrode.

Figure 2:
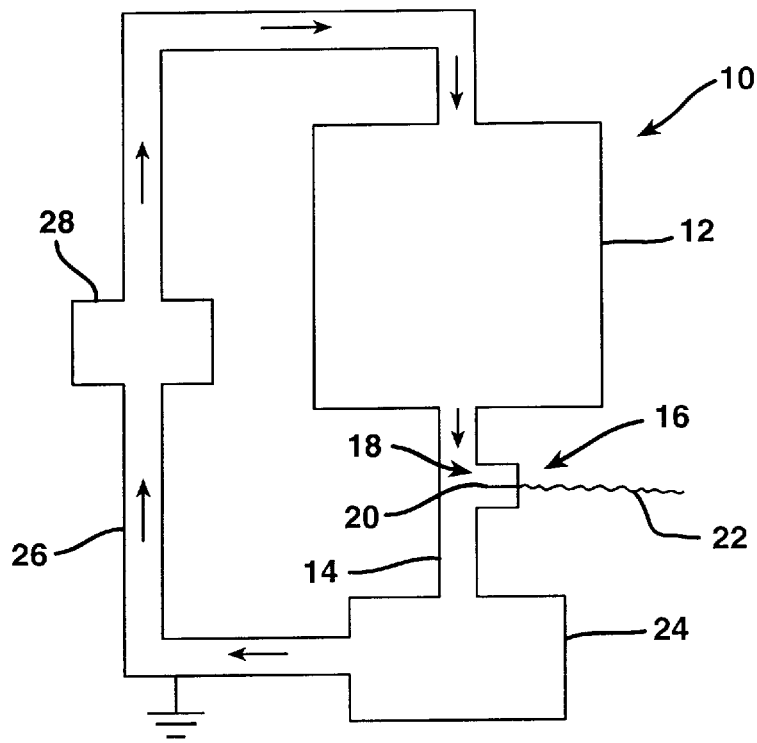
FIG. 2 is a schematic view of an on-line system involving a continuously changing sample.

FIG. 2 shows a schematic diagram of a built-in on-line system 10. System 10 includes a piece of equipment 12 through which fluid flows. The equipment 12 comprises a return line 14, a chamber 18, a reservoir 24, a circulation line 26, a fluid pump 28 and a ground. The used fluid flows through return line 14 into reservoir 24 from which it may be recirculated through line 26 by fluid pump 28. Analyzer 16 is located in chamber 18 and is, thus, permanently attached to return line 14. Analyzer 16 includes an electrode 20 and lead(s) 22. Lead(s) 22 are electrically connected to electrode 20 which extends into the fluid. Electrode 20 is electrically connected to the ground potential by the fluid.

Figure 3:
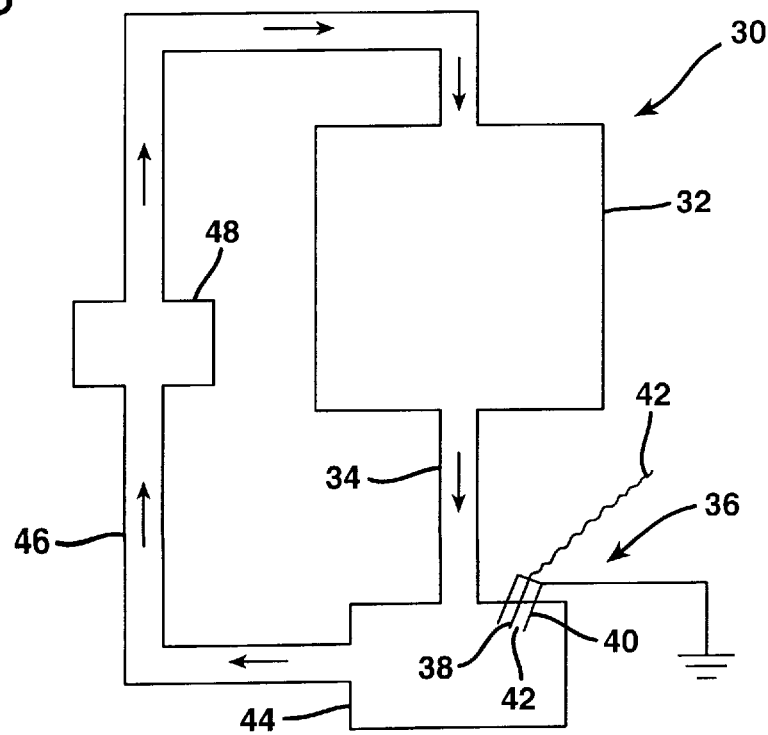
FIG. 3 is a schematic view of an on-line system involving a sample reservoir.

FIG. 3 shows a schematic diagram of a dip-stick on-line system 30. System 30 includes a piece of equipment 32 through which fluid flows. The equipment 32 comprises a return line 34, a reservoir 44, a circulation line 46 and a fluid pump 48. The used fluid flows through return line 34 into reservoir 44 from which it may be recirculated through line 46 by fluid pump 48. Analyzer 36 comprises electrode 38, a housing 40 and lead(s) 42. Electrode 38 is electrically connected to lead(s) 42. Housing 40 is electrically connected to a ground potential. Analyzer 36 is inserted into an opening in reservoir 44 for analysis. Once analyzer 36 is inserted into the opening in reservoir 44, electrode 38 comes into contact with the fluid and becomes electrically connected by the fluid to housing 40 which in turn is electrically connected to the ground potential. Analyzer 36 may be removed after the analysis is completed and replaced by a normal dip-stick or the opening may be capped.

Figure 4:
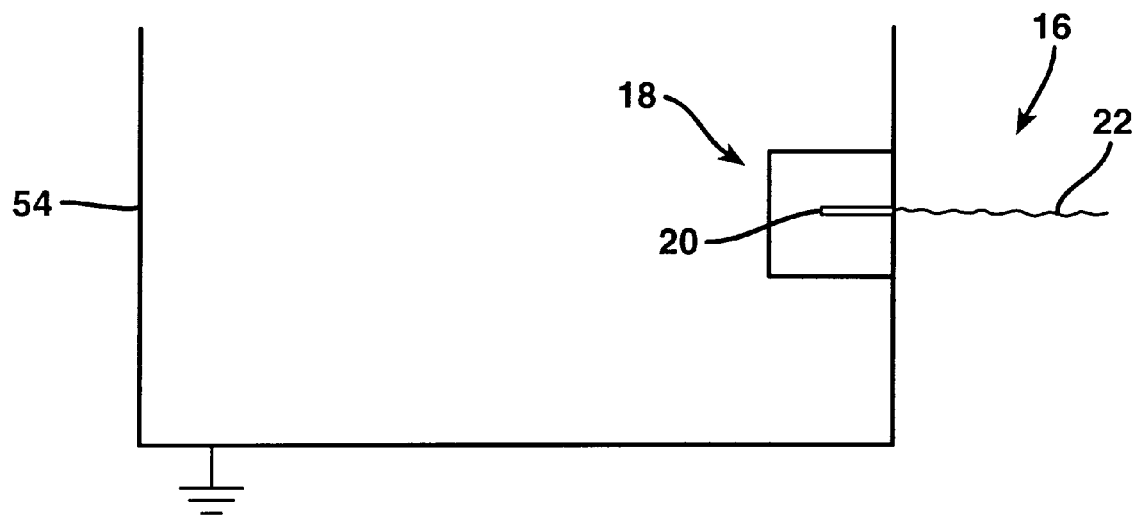
FIG. 4 is a schematic view of an on-line system involving a use container.

FIG. 4 shows in schematic form a built-in system, similar to that shown in FIG. 2, in which like numerals are used, except that the sample need not be continuously changing and there need not be a return line. Rather analyzer 16 could be placed in chamber 18 on the side of an use container 54, such as a deep fryer or gear box, connected to lead(s) 22. The configuration of analyzer 16 depends upon whether container 54 is electrically connected to a ground potential. If it is connected to a ground potential, then analyzer 36 will include a single electrode 20 as illustrated in FIG. 4. However, if container 54 is not electrically connected to a ground potential, then analyzer 16 will include a housing (not shown), similar to the one shown in FIG. 3, which will be connected to a ground potential.

Electrodes 20 and 38 should have a surface area of more than 0.01 mm$^2$. The sizes for electrodes 20 and 38 are limited solely by the size constraints of the equipment in which electrodes 20 and 38 are being used. Electrodes 20 and 38 can be comprised of any metal material which conducts an electric current. Suitable conductive materials include, but are not limited to, copper, copper alloys, nickel, nickel alloys and stainless steel. Electrodes 20 and 38 may either be metal surfaces or rods. In a preferred embodiment, electrodes 20 and 38 are each a single stainless steel rod. To provide for electrical feedthrough, a polytetrafluoroethylene seal can be placed on the electrodes for use in environments which experience elevated pressures.

The power source for electrodes 20 and 38 can be derived from a power source separate from the equipment or from the power source of the equipment, provided the power source for the equipment produces a clean signal. The power source may also be a solar powered battery.

The temperature of the sample at the time of analysis, for the on-line method, can vary between a temperature below 20° C. to a temperature above 300° C. Because the conductivity of a fluid depends upon its temperature, it is necessary to determine the temperature of the fluid before beginning an analysis. Typically, the equipment includes a temperature reading device and the temperature of the fluid can be determined from that device. The conductivity of the fluid can then be calculated using the temperature-conductivity function for that particular fluid. If the temperature-conductivity function for a particular fluid is known, one can correct for the temperature of the fluid and not use a heating element to provide the fluid with a constant temperature when measuring the fluid's conductivity. Alternatively, in situations in which the equipment containing the fluid to be analyzed does not include a temperature reading device, the analyzer may include a heating element, if one is necessary, to provide the fluid with a constant temperature.

To perform this method off-line, a sample of the used fluid is removed from the system. The analyzer is then placed in the sample and the analysis is performed. No electrolyte or solvent need be added to the sample. In this situation, the analyzer includes an electrode and a housing which is electrically connected to a ground potential. The results are analyzed the same way as the on-line method.

Because a single electrode has a high signal-to-noise ratio, the method of this invention can be used in high resistance and high noise environments in which conventional high conductivity probes fail to function. Such environments include aircraft and heavy equipment engines and systems. Additionally, the component size of the electronics used in this invention are of such a size that they can placed in a small enclosure immediately adjacent to the electrode. This also lowers the noise level.

The present invention is useful for monitoring low conductivity organic fluids with little or no water content. The invention can be used to analyze such organic fluids as fuel oils, lubricating oils, lubricating fluids, transmission fluids, coolants, hydraulic fluids and cooking oils. Typical coolants include freon, ethylene glycol and mineral oil. The present invention can be used to monitor fluids in many different applications, for example, gas turbine engines, combustion engines, transmission systems, hydraulic systems, gear boxes, operating machinery and deep fryers such as those frequently used in restaurants. Other uses and applicable fluids will be apparent to those skilled in the art.

One skilled in the art will appreciate that the invention is not limited to the precise method and apparatus described herein, and that changes can be made to this apparatus and method without departing from the scope of the invention, which is defined in the appended claims.

What is claimed is:

1. A method for analyzing and evaluation fluids which are subject to degradation and/or contamination comprising the steps of:

bringing a single electrode into contact with a sample of a fluid to be analyzed such that the electrode is electrically connected to the ground potential by the fluid;

applying a square voltage wave form to the electrode at a predetermined scan range and scan rate to cause a current to flow between the electrode and ground potential;

maintaining the scan range between about +20V and about −20V to ensure that the monitored current is based entirely on the conductivity of the fluid;

intermittently or continuously monitoring the current at the single electrode to determine a current output signal; and using the current output signal to measure the conductivity of the fluid and determine the remaining useful life thereof.

2. The method of claim 1 wherein the scan range is about +10V to about −10V.

3. The method of claim 2 wherein the scan rate is a value selected from about 1 to about 100 Hertz.

4. The method of claim 3 wherein the step of bringing the electrode into contact with the sample includes the step of attaching the electrode on-line.

5. The method of claim 4 further including the step of comparing the measured conductivity of the fluid with a known conductivity value for the fluid to determine the remaining useful life for the fluid and/or whether the fluid is contaminated.

6. The method of claim 5 wherein the fluid is selected from the group consisting of fuel oils, lubricating oils, lubricating fluids, transmission fluids, coolants, hydraulic fluids and cooking oils.

7. The method of claim 3 wherein the step of monitoring the current is done continuously.

8. The method of claim 3 wherein the step of monitoring the current is done intermittently.

9. The method of claim 1 wherein the step of bringing the electrode into contact with the sample includes the step of placing the electrode in an on-line sample reservoir and the method also includes the additional step of removing the electrode from the sample reservoir when the analysis is concluded.

10. The method of claim 1 wherein the electrode is a single stainless steel rod.

11. A method for analyzing and evaluating fluids which are subject to degradation and/or contamination comprising the steps of:

attaching a single electrode on-line and in contact with a sample of a fluid to be analyzed such that the single electrode is electrically connected to the ground potential by the fluid;

applying a square voltage wave form to the single electrode at a scan range of about ±10V to ensure that the monitored current is based entirely on the conductivity of the fluid and at a scan rate which is a single value selected from about 1 to about 100 Hertz, the square voltage wave form being applied to cause a current to flow between the single electrode and the ground potential;

intermittently or continuously monitoring the current at the single electrode to determine a current output signal; and using the current output signal to measure the conductivity of the fluid and determine the remaining useful life thereof.

12. The method of claim 11 further including the step of comparing the measured conductivity of the fluid with a known conductivity value for the fluid to determine the remaining useful life of the fluid and/or whether the fluid is contaminated.

13. The method of claim 12 wherein the fluid is selected from the group consisting of fuel oils, lubricating oils, lubricating fluids, transmission fluids, coolants, hydraulic fluids and cooking oils.

14. The method of claim 11 wherein the electrode is a single stainless steel rod.

* * * * *